(12) United States Patent
Van Hoeve et al.

(10) Patent No.: US 10,363,539 B2
(45) Date of Patent: Jul. 30, 2019

(54) SYSTEM AND METHOD FOR CONTROLLED MANUFACTURING OF MONO-DISPERSE MICROBUBBLES

(71) Applicant: Tide Microfluidics B.V., Enschede (NL)

(72) Inventors: Willem Van Hoeve, Enschede (NL); Richard Petrus Hogervorst, Enschede (NL)

(73) Assignee: Tide Microfluidics B.V., Enschede (NL)

( * ) Notice: Subject to any disclaimer, the term of this patent is extended or adjusted under 35 U.S.C. 154(b) by 197 days.

(21) Appl. No.: 15/544,828

(22) PCT Filed: Jan. 22, 2016

(86) PCT No.: PCT/NL2016/050051
§ 371 (c)(1),
(2) Date: Jul. 19, 2017

(87) PCT Pub. No.: WO2016/118010
PCT Pub. Date: Jul. 28, 2016

(65) Prior Publication Data
US 2018/0008951 A1 Jan. 11, 2018

(30) Foreign Application Priority Data
Jan. 22, 2015 (NL) ........................................ 2014178

(51) Int. Cl.
*B01F 3/04* (2006.01)
*B01J 19/00* (2006.01)
(Continued)

(52) U.S. Cl.
CPC ......... *B01J 19/0093* (2013.01); *A61K 49/223* (2013.01); *B01F 3/04106* (2013.01); *B01F 3/04503* (2013.01); *B01F 3/2057* (2013.01); *B01F 13/0062* (2013.01); *B01F 15/00162* (2013.01); *B01F 15/00357* (2013.01); *B01J 4/008* (2013.01); *B01J 4/02* (2013.01);
(Continued)

(58) Field of Classification Search
CPC .............................. B01F 3/04; B01F 3/04106
USPC .................................................... 261/30, 76
See application file for complete search history.

(56) References Cited

U.S. PATENT DOCUMENTS

| | | |
|---|---|---|
| 5,562,893 A | 10/1996 | Lohrmann |
| 2013/0014828 A1 | 1/2013 | Kim et al. |
| 2014/0220207 A1 | 8/2014 | Page et al. |

FOREIGN PATENT DOCUMENTS

| | | |
|---|---|---|
| CN | 203693432 U | 7/2014 |
| EP | 2223740 A2 | 9/2010 |

(Continued)

*Primary Examiner* — Robert A Hopkins
(74) *Attorney, Agent, or Firm* — Bret E. Field; Bozicevic, Field & Francis LLP

(57) ABSTRACT

The present invention is related to a system and method for controlled manufacturing of mono-disperse microbubbles. According to the invention, the mono-disperse nature of the collection of generated microbubbles can be improved by releasing the pressurized gaseous medium used in the system using release valve units. This further allows the system to be embodied as a portable system. In turn, the operator of an ultrasound imaging apparatus may use the system according to the invention to generate microbubbles on a patient-by-patient basis.

17 Claims, 4 Drawing Sheets

(51) Int. Cl.
 *B01J 4/00* (2006.01)
 *B01J 4/02* (2006.01)
 *B01F 13/00* (2006.01)
 *A61K 49/22* (2006.01)
 *B01F 3/20* (2006.01)
 *B01F 15/00* (2006.01)

(52) U.S. Cl.
 CPC .......... *B01F 2215/0034* (2013.01); *B01F 2215/0431* (2013.01); *B01J 2219/00894* (2013.01); *B01J 2219/00909* (2013.01); *B01J 2219/00972* (2013.01)

(56) References Cited

FOREIGN PATENT DOCUMENTS

| | | | | |
|---|---|---|---|---|
| JP | 2008290011 A | * | 12/2008 | ............ Y02W 10/15 |
| WO | WO2013141695 A1 | | 9/2013 | |

* cited by examiner

SYSTEM AND METHOD FOR CONTROLLED MANUFACTURING OF MONO-DISPERSE MICROBUBBLES

The present invention is related to a system and method for controlled manufacturing of mono-disperse microbubbles.

Using microbubbles to increase the contrast in ultrasound imaging is known in the art. These bubbles have a high degree of echogenicity, which is the ability of an object to reflect the ultrasound waves. The bubbles are administered intravenously allowing for instance the blood flow through organs to be visualized with high contrast.

Within the context of the present invention, microbubbles are bubbles having a diameter below 10 micrometer and preferably in the range of 2-5 micrometer. Bubbles with larger diameters may not safely flow through the smallest capillaries of a patient's blood vessel system and provoke oedema. On the other hand, smaller bubbles may possess poor ultrasound reflectivity.

Microbubbles generally comprise a shell that is filled by a gas core. The combination of the gas core and the shell determine the resonance frequency of the microbubble. When the microbubble is subjected to an ultrasound wave of a suitable frequency, equaling or at least approaching the resonance frequency of the microbubble, the bubble will resonate at the resonance frequency of the microbubble. This resonance can be picked up by the ultrasound imaging apparatus. In this manner, a high contrast can be achieved between microbubble-rich and microbubble-poor regions.

A microbubble generation unit is known from WO 2013/141695. The contents of this patent application are hereby incorporated by reference, for all purposes. The known unit comprises a chip having a first inlet for receiving a dispersed phase fluid, a second inlet for receiving a continuous phase fluid, and a bubble formation channel in which microbubbles are generated using the received dispersed phase fluid and the received continuous phase fluid.

At least one of the dispersed phase fluid and the continuous phase fluid may contain a surfactant suitable for populating a fluid interface between the dispersed phase fluid and the continuous phase fluid, and to thus encapsulate and stabilize the bubbles of the dispersed phase fluid within the continuous phase fluid upon formation, to thereby prevent the dissolution of the bubbles in the continuous phase fluid. The surfactant may, for example, include a film-forming (mixture of) phospholipid(s), e.g. a mixture of DPPC, DPPA, and DPPE-PEG5000.

The known unit, schematically illustrated as microbubble generation unit 1 in FIG. 1, comprises two inlets 2, 2' through which the continuous phase fluid is fed and an inlet 3 through which the dispersed phase fluid is fed. Inlets 2, 2' are in fluid communication with each other. Most often, a single inlet can be used, hereafter denoted as inlet 2, after which the inputted fluid can be split over the respective upper and lower channels in FIG. 1.

Due to the bends in the upper and lower channel, the continuous phase fluid impinges onto the dispersed phase fluid from two opposite sides. It thereby shapes and confines the flow of the dispersed phase fluid such that bubbles or droplets 4 of the dispersed phase fluid are formed in the continuous phase fluid inside a bubble formation channel 5. Bubbles 4 are essentially created one after the other.

Bubble formation channel 5 in FIG. 1 has a rectangular cross section, having a width in the range of 15-35 micrometer, a height in the range of 10-30 micrometer, and a length in the range of 50-1000 micrometer.

For ultrasound imaging, the size and quantity of the bubbles is of utmost importance. The size of the bubbles determines their resonance frequency and thereby their acoustic properties, whereas the quantity of bubbles should be sufficient to achieve suitable contrast while not causing health risks for the patient.

During ultrasound examination, the operator of the ultrasound imaging apparatus determines the desired frequency of the ultrasound waves with which the examination should be performed. This frequency is determined by the depth of the tissue to be analysed as well as the type of tissue.

To achieve a suitable contrast, it is desired that the resonance frequency of the microbubbles corresponds to the desired frequency. Moreover, the variance in resonance frequencies among the microbubbles should be sufficiently low.

Microbubbles that essentially display the same resonance frequencies are referred to as mono-disperse microbubbles. The term 'mono-disperse', where used in this text to characterize a collection of microbubbles, may be construed to mean that the poly-dispersity index (PDI) of the collection, mathematically defined as $PDI=s/n$, wherein n denotes the average bubble radius and s the standard deviation of the bubble radii, is smaller than $5\times10^{-2}$. That is, a collection of bubbles having a PDI<5% may be considered to be mono-disperse.

In the art, microbubbles are mass-produced prior to the ultrasound examination without taking into consideration the desired frequency that is determined as part of the ultrasound imaging procedure on a patient-by-patient basis. Hence, the operator of the ultrasound imaging apparatus must tune the frequency of the ultrasound waves to the acoustic properties of the microbubbles supplied to him. Moreover, mass-produced microbubbles most often display a large variance in the size distribution of the microbubbles. Hence, the ultrasound imaging procedure cannot be optimally performed.

A known method for operating the abovementioned known microbubble generation device 1 is shown in FIG. 2. Here, inlet 2 is connected to a liquid pressurization unit 6 which comprises a liquid 7 that is held in a container. A first pressure regulated gaseous medium is fed to liquid pressurization unit 6. This medium originates from a first source 8 and is pressure regulated by means of a first pressure regulation unit 9. First source 8 can be in the form of a gas cylinder in which the first gaseous medium is held under a pressure that normally exceeds the pressures encountered in the remaining part of the system. A conduit from pressure regulation unit 9 extends to above the liquid-gaseous medium interface, whereas a further conduit extends from below the liquid-gaseous medium interface to inlet 2 of microbubble generation unit 1. Consequently, the first pressure regulated gaseous medium is used to push, by means of its pressure, liquid 7 towards inlet 2.

Inlet 3 receives a second pressure regulated gaseous medium from a second source 10 via a second pressure regulation unit 11.

The size and quantity of the microbubbles is determined by the pressure of the first pressure regulated gaseous medium and the pressure of the second pressure regulated gaseous medium. These pressures can be set by means of pressure regulation units 9, 11 and allow an operator to produce microbubbles having the desired properties.

In the example in FIG. 2, a liquid is supplied to inlet 3, which corresponds to the continuous phase fluid, whereas a gaseous medium is supplied to inlet 2 of microbubble generation unit 1. Consequently, gas bubbles are formed in the liquid.

The system illustrated in FIG. 2 is typically used to produce large quantities of microbubbles, far exceeding that which is needed for a single ultrasound imaging procedure. The applicant has found that this system is not suitable for producing a limited amount of mono-disperse microbubbles targeted at a user-definable ultrasound imaging frequency.

US 2014/220207 A1 discloses a system for dissolving a gaseous medium in a liquid under pressure. Once the pressurized liquid is brought back to atmospheric pressure, bubbles are generated. However, this generation is not uniform in the sense that bubble diameters will vary strongly. Moreover, the bubbles that are generated do not classify as microbubbles. In this known system, release valves are used to quickly release the stream of the liquid.

CN 203 693 432 U discloses a high pressure shower in which pressurized liquid is fed to a cylinder. Inside this cylinder, a gaseous medium is dissolved in the liquid. This system generates bubbles having a diameter of roughly 50 micrometers, thereby not qualifying as microbubbles. According to this document, release valves can be connected to the inlets for the pressurized liquid to quickly release the stream of liquid to the shower.

An object of the present invention is to provide a system that is suitable for producing a limited amount of mono-disperse microbubbles targeted at a user-definable ultrasound imaging frequency. This object has been reached by a system for controlled manufacturing of microbubbles that comprises a microbubble generation unit having a first inlet for receiving a dispersed phase fluid, a second inlet for receiving a continuous phase fluid, and a bubble formation channel in which microbubbles are generated using the received dispersed phase fluid and the received continuous phase fluid. According to the invention, the first inlet and the second inlet are connected to a source of a first pressure regulated gaseous medium and to a source of a second pressure regulated gaseous medium, respectively. The respective sources are connected, independently from each other, either directly or via a respective liquid pressurization unit. Such liquid pressurization unit has an inlet for receiving the respective pressure regulated gaseous medium and is configured for outputting a flow of a respective pressurized liquid to the respective inlet of the microbubble generation unit in dependence of a flow and/or pressure of the received respective pressure regulated gaseous medium. Moreover, at least one of the first inlet and the second inlet is connected to the respective source of the respective pressure regulated gaseous medium via a respective liquid pressurization unit.

The present invention is characterized in that the system comprises a first release valve unit that is configured for releasing the first pressure regulated gaseous medium, a second release valve unit that is configured for releasing the second pressure regulated gaseous medium, and a control unit for controlling the first and second release valves in dependence of a comparison between a pressure of the first pressure regulated gaseous medium and a first pressure setting and between a pressure of the second pressure regulated gaseous medium and a second pressure setting, respectively.

The applicant has found that a main cause for poly-disperse microbubbles is related to the end of the microbubble generation process. In the system illustrated in FIG. 2, the generation process is stopped by providing low values, such as 0 bar, as pressure settings to the two pressure regulation units. The microbubble generation unit is a relatively small device in the form of a chip. Consequently, the internal volume in the microbubble generation unit that is used by the dispersed phase fluid and the continuous phase fluid is very limited, e.g. microliters or less. Hence, when the control unit provides the low value pressure setting to the pressure regulation units, pressure in the system, including the internal volume in the liquid pressurization unit 6, and most importantly, the internal volume occupied by the gaseous medium in the liquid pressurization unit, which is relatively large, e.g. 1-100 ml, will drop only very slowly. During this time, the microbubble generation process continues. For instance, in case the pressure has started at a relatively high value, and is slowly decreasing to a low value to stop the process, microbubbles will be generated with varying diameters. For example, it is possible that microbubbles will be created with decreasingly smaller diameters, depending on which of the pressures of the first and second pressure regulated gaseous medium drops the fastest. It is noted that the microbubble size is proportional to the gas-to-liquid flow rate ratio, wherein the flow rate is proportional to applied pressure and flow resistance in the channel. An important aspect of prior art approaches is that during the stopping procedure, the size of the microbubbles is not controlled and a source of poly-dispersity is created.

In case the system in FIG. 2 is used for mass producing microbubbles for a large number of patients, the mono-dispersive nature of the entire collection of microbubbles will only be affected to a very limited extent by the above-mentioned process. This is due to the fact that the time during which microbubbles were generated at stable pressures is much larger than the time that is required to shut down the microbubble generation process. However, when microbubbles are to be generated for a single patient only, this no longer holds.

According to the invention, this problem is solved by using a first release valve unit for releasing the first pressure regulated gaseous medium, and a second release valve unit for releasing the second pressure regulated gaseous medium. These release valve units, when opened, allow the first and second pressure regulated gaseous medium to be evacuated at relatively high flow rates. Hence, the pressure of the first and/or second pressure regulated gaseous medium inside the container of the liquid pressurization unit can be reduced to a very low level almost instantaneously, causing the flow of liquid to the microbubble generation unit to be stopped almost directly. This is in contrast to arranging a release valve coupled to the outlet of the liquid pressurization unit. Even if such a valve was used, and if this valve was opened, the pressurized gaseous medium inside the liquid pressurization unit would still press the liquid towards the microbubble generation unit. Due to the viscosity of the liquid, the release valve would be unable to pass a sufficient amount of liquid through its opening to prevent liquid entering the microbubble generation unit. Similarly, the first and/or second pressure regulated gaseous medium that is already in the microbubble generation unit as well as the first and/or second pressure regulated gaseous medium in the conduit between the pressure regulation unit(s) and the microbubble generation unit can be evacuated almost instantaneously.

Using these release valves thereby offers the possibility to more quickly stop the generation of microbubbles. Consequently, the time in which microbubbles are generated at relatively constant pressures can be reduced while still maintaining an acceptable mono-dispersive nature of the collection of generated microbubbles. This in turn means that the system according to the present invention can be used to generate patient-specific microbubbles in a short amount of time, typically within minutes. It can therefore be embodied as a portable system allowing the generation of microbubbles near the ultrasound imaging apparatus itself. This offers more convenience and flexibility for the operator of the ultrasound imaging apparatus and improves the final imaging result as the operator is able to choose the microbubble size on a patient-by-patient basis.

According to the invention, the source of the first pressure regulated gaseous medium may be connected to the first inlet directly and the source of the second pressurized gaseous medium may be connected to the second inlet via a liquid pressurization unit. Alternatively, the sources of the first and second pressure regulated gaseous medium may be each connected via a respective liquid pressurization unit to the first and second inlet, respectively, wherein the respective liquids outputted by the respective liquid pressurization units are different. Consequently, microbubbles having a core filled with a gaseous medium and dispersed in a liquid may be formed. However, the present invention does not exclude the formation of microbubbles having a core filled with a first liquid medium and dispersed in a second liquid.

The control unit may be configured to control the first release valve unit for releasing the first pressure regulated gaseous medium if the pressure of the first pressure regulated gaseous medium is larger than the first pressure setting by a first predefined amount or ratio. Additionally or alternatively, the control unit may be configured to control the second release valve unit for releasing the second pressure regulated gaseous medium if the pressure of the second pressure regulated gaseous medium is larger than the second pressure setting by a second predefined amount or ratio. For example, if the first pressure setting is 3 bar, the first release valve unit may be controlled if the pressure of the first pressure regulated gaseous medium exceeds 3 bar by a predefined amount, such as 0.2 bar, or by a predefined ratio such as 1.05. In the former case, the release valve will release the first gaseous medium when the pressure exceeds 3.2 bar, whereas in the latter case, the release valve will release the first gaseous medium when the pressure exceeds 3.0×1.05=3.15 bar. This may be advantageous during the start of the microbubble generation process in which pressure has to be build up very quickly. The combination of the low volume inside the system and the high flow rates may cause pressure overshoot to occur in the system. Furthermore, the low volume implicates that pressure stabilization may take some time. By using release valves, a damping of the oscillatory behaviour of the pressure can be realized, thereby reducing the time during which the pressure is insufficiently stabilized. This will further improve the monodispersive nature of the collection of generated microbubbles. As stated above, this is particularly important in situations wherein microbubbles are generated on a patient-by-patient basis.

The system may further comprise a first container holding the first gaseous medium under pressure, such as a gas cylinder, and a first pressure regulation unit, wherein the first pressure regulation and the first container form the source of the first pressure regulated gaseous medium, wherein the first pressure regulation unit is configured for receiving the first gaseous medium from the first source and for outputting a pressure regulated flow of said first gaseous medium, wherein the first pressure regulation unit is configured for regulating the pressure of the outputted first gaseous medium to be equal to a first pressure setting. Similarly, the system may comprise a second container holding the second gaseous medium under pressure, such as a gas cylinder, and a second pressure regulation unit, wherein the second pressure regulation and the second container form the source of the second pressure regulated gaseous medium, wherein the second pressure regulation unit is configured for receiving the second gaseous medium from the second source and for outputting a pressure regulated flow of said second gaseous medium, wherein the second pressure regulation unit is configured for regulating the pressure of the outputted second gaseous medium to be equal to a second pressure setting.

The first and second pressure regulation unit may each comprise a pressure sensor and a pressure controller for controlling the pressure of the outputted first or second gaseous medium in dependence of the measured pressure and the first pressure setting or second pressure setting, respectively. Furthermore, the system may comprise a biological filter arranged downstream of the first and/or second pressure regulation unit and upstream of the liquid pressurization unit(s), if any, wherein the biological filter is configured to remove bacteria from the first and/or second pressure regulated gaseous medium.

The advantage of using a pressure regulation unit in combination with a liquid pressurization unit, instead of using a pump to supply liquid to the microbubble generation unit, is that this approach allows the separation between the flow of liquid and the flow of gaseous medium, wherein the latter comes into contact with mechanical components that are difficult to sterilize or to maintain sterilized. By using a filter downstream of the pressure regulation unit, bacteria added to the gaseous medium when traversing the pressure regulation unit can be removed prior to the moment when the liquid and the gaseous medium come into contact with each other. Hence, the liquid does not become contaminated by the gaseous medium exiting the pressure regulation unit.

The first and second pressure regulation units may be configured to output, to the control unit, the measured pressure of the first or second pressure regulated gaseous medium, respectively, or a comparison signal between the first or second pressure setting and the measured pressure of the first or second pressure regulated gaseous medium, respectively. Using the outputted signal, the control unit may appropriate control the various components in the system. For instance, the control unit may compare the relevant pressure setting to the relevant measured pressure. Alternatively, the comparison is performed by the pressure regulation unit which has received the pressure setting from the control unit.

The first and/or second release valve unit may comprise a low-flow rate release valve and a high-flow release valve, which valves are arranged in parallel. This allows the possibility to release the first and/or second gaseous medium at a relatively low and high flow rate. The former being advantageous if only a relatively small pressure difference needs to be achieved. Furthermore, it allows for a dual step approach, wherein first a coarse step is implemented using only the high-flow rate release valve, and then a fine step is implemented using only the low-flow rate release valve.

The system may further comprise an input unit for inputting the first and second pressure setting, and for inputting a desired number of microbubbles to be generated and/or a desired bubble generation time.

The system may further be operable in a start-up state in which the pressure of the first pressure regulated gaseous medium and/or the pressure of the second pressure regulated gaseous medium vary and a steady state wherein these pressures are substantially constant. The control unit may be configured to set a respective low value as the first pressure setting and the second pressure setting in order to control the first and second release valve units for releasing the first and second pressure regulated gaseous medium, respectively, when the desired number of microbubbles has been generated and/or when a time duration of the steady state and/or a combined time duration of the start-up state and steady state exceeds the desired bubble generation time.

Further to the above, the input unit may further be configured for inputting a further first pressure setting and a further second pressure setting and for inputting a further desired number of microbubbles to be generated and/or a further desired bubble generation time, wherein the system may further be operable in a further steady state, following the earlier steady state, in which the further first and second pressure setting and the further desired number of microbubbles to be generated and/or a further desired bubble generation time are used by the control unit for controlling the first and second release valves, and, preferably, the first and second pressure regulation units. For example, the further pressure setting may be 2.5 bar, following an initial pressure setting of 3.0 bar. In addition to or in place of instructing the pressure regulation units to regulate the pressure from 3.0 bar to 2.5 bar, the release valve units may be controlled. Consequently, a quick change in pressure may be achieved. This feature may for instance be useful if a bi-dispersive collection of microbubbles is desired. Such collection may be useful if the ultrasound imaging procedure targets two different types of tissue simultaneously.

The system may further comprise a bubble counting unit for counting the number of generated bubbles and/or a timer for timing the start-up state and/or the steady state. In an embodiment, at least the bubble formation channel may be transparent to a measuring wavelength. In this case, the bubble counting unit may comprise a light source for emitting light at the measuring wavelength, and a light detector responsive to light of the measuring wavelength, wherein the light source is configured to emit said light through the bubble formation channel and wherein the light detector is configured to detect the light that has passed through the bubble formation channel. The bubble counting unit may be configured to count the number of generated bubbles in dependence of the detected light. As an example, the detection of microbubbles may be based on the adsorption or diffraction of light by the microbubbles. Due to the fact that microbubbles are generated one after the other in the bubble formation channel it is possible to individually count them. The bubble counting unit may also include a lens system to create a line-shaped light beam. The light beam is directed at the bubble formation channel. The light beam is perpendicular to the microbubble flow direction.

The first and second pressurized gaseous medium may be identical. As such, a single container, e.g. gas cylinder, may be used for both the first and second gaseous medium. In an embodiment, the first and/or second gaseous medium comprises at least one from the group consisting of $SF_6$, $N_2$, $CO_2$, $O_2$, ambient air, and perfluorocarbon gases, such as $C_3F_8$ or $C_4F_{10}$. Additionally or alternatively, the liquid in the liquid pressurization unit(s) comprises at least one from the group consisting of water, dispersion of lipids, such as phospholipids, or proteins in an aqueous solution, active pharmaceutical ingredients, and alcohols.

The first and/or second release valve unit may be configured to release the first or second pressure regulated gaseous medium to a reservoir or to an outside environment, such as open air. Here, the low volume of the system is particularly important as most of the types of gasses used for the generation of microbubbles have a detrimental effect on human health when released in large quantities.

According to a second aspect, the present invention provides a method for controlled manufacturing of microbubbles, comprising the steps of:

providing a system as defined above;

supplying the first pressure regulated gaseous medium and the second pressure regulated gaseous medium to thereby generate microbubbles using the provided microbubble generation unit;

counting a number of generated microbubbles and determining that the generation of microbubbles should be stopped if sufficient microbubbles have been generated and/or if the microbubbles have been generated during a sufficient amount of time.

According to the invention, the method is characterized by releasing the first and second pressurized gaseous medium using the first and second release valve unit, respectively, if it has been determined that the generation of the microbubbles should be stopped.

Next, the invention will be described in more detail referring to the appended drawings, wherein identical reference numbers have been used to designate identical or similar components, and wherein.

Figure 1:
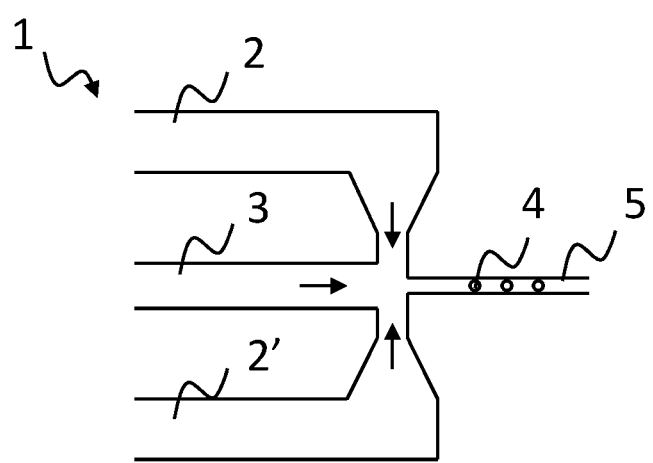
FIG. 1 illustrates a microbubble generation unit known from the art.
Figure 2:
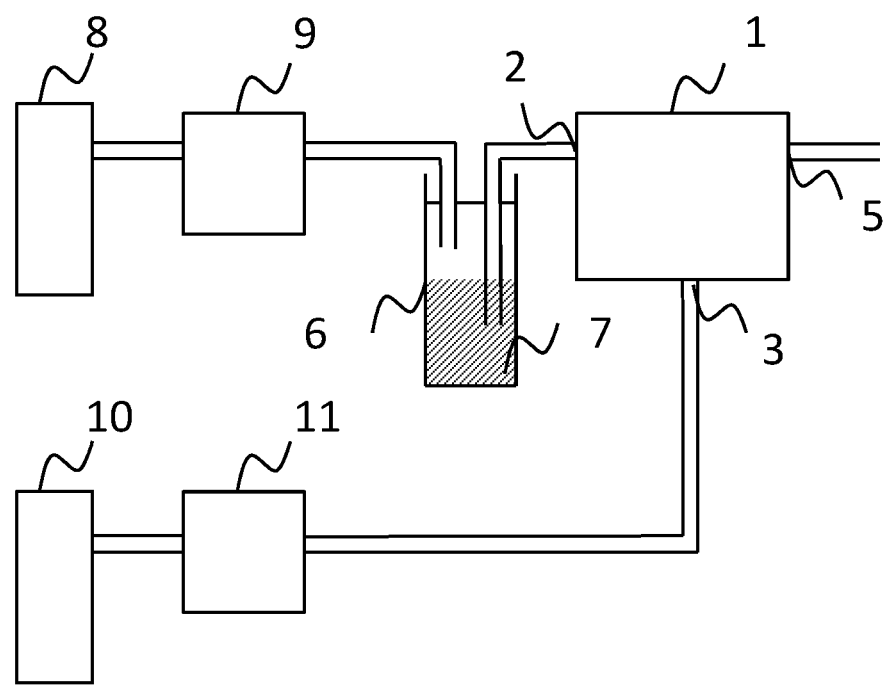
FIG. 2 illustrates a known system for generating microbubbles using the microbubble generation unit illustrated in FIG. 1.
Figure 3:
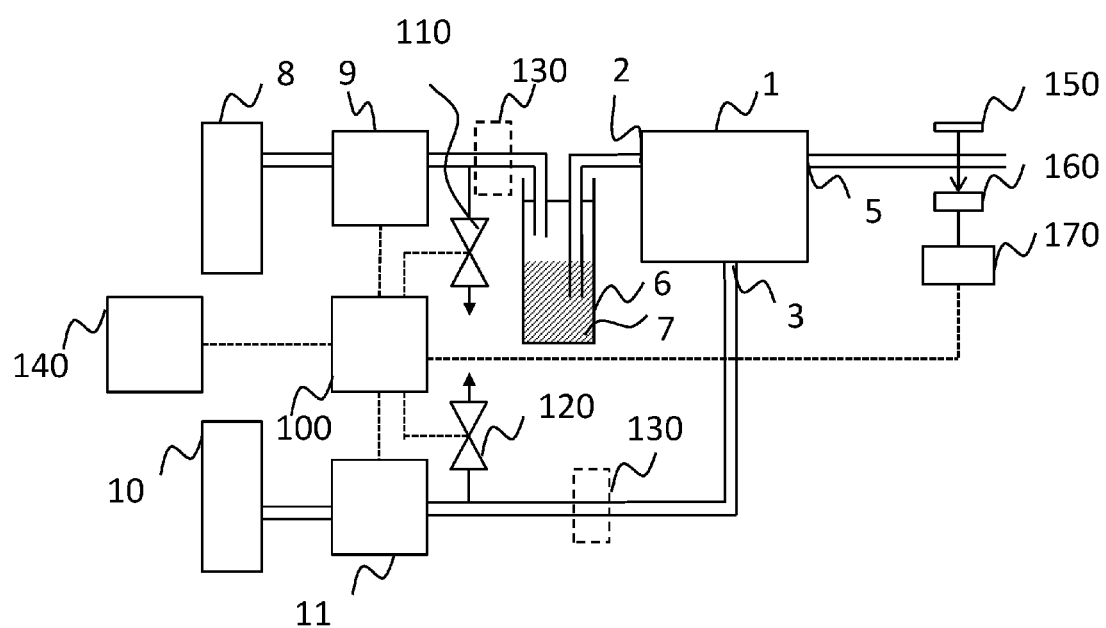
FIG. 3 illustrates an embodiment of a system for generating microbubbles in accordance with the present invention.

FIG. 3 illustrates an embodiment of a system for generating microbubbles in accordance with the present invention. This embodiment comprises the system as illustrated in FIG. 2 having the microbubble generation unit of FIG. 1. However, a control unit 100 has been added that controls two release valve units 110, 120, which may each comprise one or more release valves suitable for high and/or low flow rates. Control unit 100 controls release valve units 110, 120 and pressure regulation units 9, 11. The system further comprises an input unit 140 by means of which a user may input process parameters, such as the desired number of generated microbubbles, the time during which the microbubbles should be generated and the pressure level for the first pressure regulated gaseous medium and the second pressure regulated gaseous medium. Filters 130 are arranged to remove bacteria from the gaseous medium after it leaves the pressure regulation units 9, 11.

Figure 4:
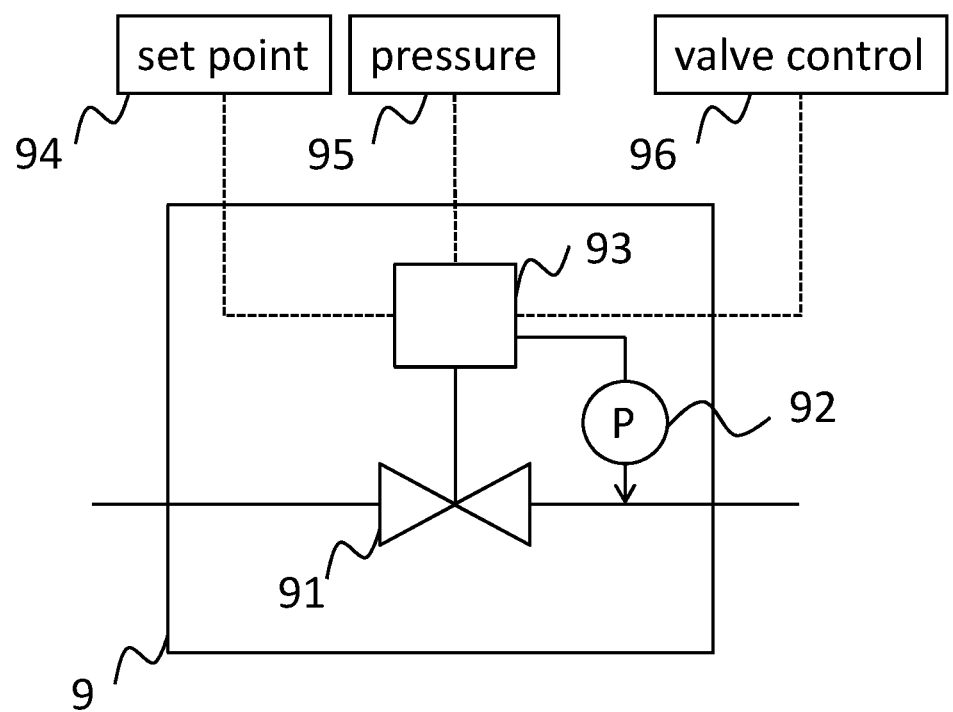
FIG. 4 illustrates a pressure regulation unit used in the system depicted in FIG. 3.

The operation of the system in FIG. 3 will now be explained by referring to FIGS. 3 and 4. At the start of the microbubble generation process, first gaseous medium and second gaseous medium are supplied from gas cylinders 8, 10, respectively. If required, pressure relief valves may be used to minimize the risk of exposing the system to overpressures. Because, the pressure in these cylinders is typically too large, the pressure is regulated by pressure regulation units 9, 11.

A user has entered the relevant process parameters using input unit 140. This information is fed to control unit 100, which then supplies the relevant pressure settings to the pressure regulation units 9, 11. Each pressure regulation unit comprises a control valve 91 for regulating the pressure, a pressure sensor 92 for measuring the pressure of the outputted gaseous medium, and a pressure controller 93, which controls control valve 91 in dependence of the measured pressure, see FIG. 4.

Pressure regulation unit 9, 11 outputs the measured pressure 95. Furthermore, it receives a pressure setting 94 from control unit 100. Pressure regulation units 9, 11 are configured for regulation the relevant pressure in dependence of the pressure setting received from control unit 100.

During the start-up state, the pressure setting is generally much larger than the existing pressures in the system. Consequently, a large flow of first and second gaseous medium is supplied from pressure regulation units 9, 11. Should an excessive amount of overshoot occur with respect to the pressure setting, then control unit 100 may control release valve units 110, 120 for releasing the excessive pressure to the outside, such as the ambient air.

In a further or alternative embodiment of pressure regulation unit 9, 11, pressure controller 93, or another control unit, is configured to output a valve control signal 96. This signal can be used to control release valves 110, 120 directly. With these embodiments of pressure regulation units 9, 11, control unit 100 may not need to control release valves 110, 120 itself.

Once the pressures have stabilized, mono-disperse microbubbles are generated within microbubble generation unit 1. If a sufficient amount of microbubbles has been generated or if microbubbles have been generated during a sufficient amount of time, determined in dependence of the parameters inputted through input unit 140, control unit 100 will send a low value as pressure setting to pressure regulation units 9, 11, such as 0 bar. In addition, it will control release valve units 110, 120 for releasing the first and second gaseous medium to the outside. This control may alternatively be performed by the pressure regulation units 9, 11 via valve control signal 96, if such functionality is implemented in the pressure regulation units 9, 11. Consequently, the process of generating microbubbles can be stopped very quickly. The amount of microbubbles having an undefined or unpredictable size can thereby be minimized.

FIG. 3 illustrates how a light source 150 is used in combination with a light detector 160. Here, light source 150 is a laser that emits light having a wavelength in the range between 495 nm and 700 nm, although other wavelength ranges are not excluded. Light detector can be embodied as a photodiode. Once a microbubble passes through bubble formation channel 5 and intersects the light beam generated by laser 150, the intensity of the light received by photodiode 160 will drop, for instance because the light beam is diffracted by the microbubbles. A processing unit 170 can be used for counting the microbubbles. For instance, processing unit 170 may increment a counter value every time a falling edge is detected in the measured light intensity.

In the above, the invention has been disclosed using embodiments thereof. However, the skilled person will understand that the invention is not limited to these embodiments and that many more embodiments are possible without departing from the scope of the present invention, which is defined by the appended claims.

For instance, the present invention has been applied in the field of microbubble generation for medical purposes. However, the present invention is not limited thereto. Its inventive concept may equally be applied in other fields of technology as well. More in particular, the inventive concept may also be used in other systems that use smaller or larger bubbles, but wherein it is still important to produce a limited amount of mono-disperse bubbles.

The invention claimed is:

1. A system for controlled manufacturing of microbubbles, comprising:
   a microbubble generation unit having a first inlet for receiving a dispersed phase fluid, a second inlet for receiving a continuous phase fluid, and a bubble formation channel in which microbubbles are generated using the received dispersed phase fluid and the received continuous phase fluid, wherein the bubble formation channel has a width in the range of 15-35 micrometer, and a height in the range of 10-30 micrometer;
   a liquid pressurization unit having an inlet for receiving a second pressure regulated gaseous medium from a source of said second pressure regulated gaseous medium and being configured for outputting a flow of a pressurized liquid to the second inlet of the microbubble generation unit in dependence of a flow and/or pressure of the received second pressure regulated gaseous medium, wherein the first inlet of the microbubble generation unit is connected to a source of a first pressure regulated gaseous medium;
   a first release valve unit arranged in between the source of the first pressure regulated gaseous medium and the first inlet of the microbubble generation unit and being configured for releasing the first pressure regulated gaseous medium;
   a second release valve unit arranged in between the source of the second pressure regulated gaseous medium and the inlet of the liquid pressurization unit and being configured for releasing the second pressure regulated gaseous medium; and
   a control unit for controlling the first and second release valves in dependence of a comparison between a pressure of the first pressure regulated gaseous medium and a first pressure setting and between a pressure of the second pressure regulated gaseous medium and a second pressure setting, respectively.

2. The system according to claim 1, wherein the bubble formation channel has a length in the range of 50-1000 micrometer.

3. The system according to claim 1, wherein the control unit is configured to control the first release valve unit for releasing the first pressure regulated gaseous medium if the pressure of the first pressure regulated gaseous medium is larger than the first pressure setting by a first predefined amount or ratio, and wherein the control unit is configured to control the second release valve unit for releasing the second pressure regulated gaseous medium if the pressure of the second pressure regulated gaseous medium is larger than the second pressure setting by a second predefined amount or ratio.

4. The system according to claim 1, further comprising:
   a first container holding the first gaseous medium under pressure, such as a gas cylinder, and a first pressure regulation unit, said first pressure regulation and said first container forming said source of the first pressure regulated gaseous medium, wherein the first pressure regulation unit is configured for receiving the first gaseous medium from the first source and for outputting a pressure regulated flow of said first gaseous medium, wherein the first pressure regulation unit is configured for regulating the pressure of the outputted first gaseous medium to be equal to a first pressure setting;
   a second container holding the second gaseous medium under pressure, such as a gas cylinder, and a second pressure regulation unit, said second pressure regulation and said second container forming said source of the second pressure regulated gaseous medium, wherein the second pressure regulation unit is configured for receiving the second gaseous medium from the second source and for outputting a pressure regulated flow of said second gaseous medium, wherein the second pressure regulation unit is configured for regulating the pressure of the outputted second gaseous medium to be equal to a second pressure setting.

5. The system according to claim 4, wherein the first and second pressure regulation unit each comprise a pressure sensor and a pressure controller for controlling the pressure of the outputted first or second gaseous medium in dependence of the measured pressure and the first pressure setting or second pressure setting, respectively.

6. The system according to claim 5, further comprising a biological filter arranged downstream of the first and/or second pressure regulation unit and upstream of the liquid pressurization unit(s), if any, wherein the biological filter is configured to remove bacteria from the first and/or second pressure regulated gaseous medium.

7. The system according to claim 6, wherein the first and second pressure regulation units are configured to output, to the control unit, the measured pressure of the first or second pressure regulated gaseous medium, respectively, or a comparison signal between the first or second pressure setting and the measured pressure of the first or second pressure regulated gaseous medium, respectively.

8. The system according to claim 1, wherein the first and/or second release valve unit comprises a low-flow rate release valve and a high-flow release valve, which valves are arranged in parallel.

9. The system according to claim 1, further comprising an input unit for inputting the first and second pressure setting, and for inputting a desired number of microbubbles to be generated and/or a desired bubble generation time.

10. The system according to claim 9, further comprising a bubble counting unit for counting the number of generated bubbles and/or a timer for timing the start-up state and/or the steady state.

11. The system according to claim 10, wherein at least the bubble formation channel is transparent to a measuring wavelength, the bubble counting unit comprising a light source for emitting light at said measuring wavelength, and a light detector responsive to light of said measuring wavelength, wherein said light source is configured to emit said light through the bubble formation channel and wherein the light detector is configured to detect said light that has passed through the bubble formation channel, the bubble counting unit being configured to count the number of generated bubbles in dependence of the detected light.

12. The system according to claim 1, wherein the first and/or second gaseous medium comprises at least one from the group consisting of $SF_6$, $N_2$, $CO_2$, $O_2$, ambient air, and perfluorocarbon gases, such as $C_3F_8$ or $C_4F_{10}$.

13. The system according to claim 1, wherein the liquid in the liquid pressurization unit(s) comprises at least one from the group consisting of water, dispersion of lipids, such as phospholipids, or proteins in an aqueous solution, active pharmaceutical ingredients, and alcohols.

14. The system according to claim 1, wherein the first and/or second release valve unit is configured to release said first or second pressure regulated gaseous medium to a reservoir or to an outside environment, such as open air.

15. A method for controlled manufacturing of microbubbles, comprising
providing the system as defined in claim 10;
supplying the first pressure regulated gaseous medium and the second pressure regulated gaseous medium to thereby generate microbubbles using the provided microbubble generation unit;
counting a number of generated microbubbles and determining that the generation of microbubbles should be stopped if sufficient microbubbles have been generated and/or if the microbubbles have been generated during a sufficient amount of time;
wherein
releasing the first and second pressurized gaseous medium using the first and second release valve unit, respectively, if it has been determined that the generation of the microbubbles should be stopped.

16. The method according to claim 15, wherein the system is operable in a start-up state in which the pressure of the first pressure regulated gaseous medium and/or the pressure of the second pressure regulated gaseous medium vary, and a steady state wherein these pressures are substantially constant;
the method comprising setting, by the control unit, a respective low value as the first pressure setting and the second pressure setting in order to control the first and second release valve units for releasing the first and second pressure regulated gaseous medium, respectively, when the desired number of microbubbles has been generated and/or when a time duration of the steady state and/or a combined time duration of the start-up state and steady state exceeds the desired bubble generation time.

17. The method according to claim 16, further comprising inputting, using the input unit, a further first pressure setting and a further second pressure setting and inputting a further desired number of microbubbles to be generated and/or a further desired bubble generation time, wherein the system is further operable in a further steady state, following said steady state, the method further comprising the control unit using, in said further steady state, said further first and second pressure setting and said further desired number of microbubbles to be generated and/or said further desired bubble generation time, for controlling the first and second release valve units, and, preferably, the first and second pressure regulation units.

* * * * *